(12) United States Patent
Huang et al.

(10) Patent No.: US 7,906,563 B2
(45) Date of Patent: Mar. 15, 2011

(54) POLYSILOXANE-BASED PREPOLYMER AND HYDROGEL

(75) Inventors: Ching-Ping Huang, Taoyuan Hsien (TW); Roy Wu, Taoyuan Hsien (TW); Ken-Yuan Chang, Taoyuan Hsien (TW)

(73) Assignee: Far Eastern New Century Corporation (TW)

( * ) Notice: Subject to any disclaimer, the term of this patent is extended or adjusted under 35 U.S.C. 154(b) by 290 days.

(21) Appl. No.: 12/292,929

(22) Filed: Dec. 1, 2008

(65) Prior Publication Data

US 2009/0170976 A1     Jul. 2, 2009

(30) Foreign Application Priority Data

Dec. 28, 2007   (TW) ................................ 96150791 A

(51) Int. Cl.
*C08F 290/06*     (2006.01)
*C07F 7/04*     (2006.01)

(52) U.S. Cl. ....................... 523/107; 556/413
(58) Field of Classification Search ............... 523/107; 556/413

See application file for complete search history.

(56) References Cited

U.S. PATENT DOCUMENTS

| | | | | |
|---|---|---|---|---|
| 3,895,043 A * | 7/1975 | Wagner et al. | ................. | 556/416 |
| 5,387,632 A | 2/1995 | Lai et al. | | |
| 5,902,847 A * | 5/1999 | Yanagi et al. | ................. | 524/300 |
| 6,172,152 B1 * | 1/2001 | Kim et al. | ...................... | 524/379 |
| 6,586,548 B2 | 7/2003 | Bonafini, Jr. et al. | | |
| 7,345,130 B2 * | 3/2008 | Zhu et al. | ......................... | 528/17 |
| 2001/0036554 A1 * | 11/2001 | Jin et al. | ........................ | 428/412 |
| 2005/0271885 A1 * | 12/2005 | Stanjek et al. | ................. | 428/447 |

\* cited by examiner

*Primary Examiner* — Randy Gulakowski
*Assistant Examiner* — Robert Loewe
(74) *Attorney, Agent, or Firm* — Morgan, Lewis & Bockius LLP

(57) ABSTRACT

A polysiloxane-based prepolymer of a three-dimensional network structure produced by hydrolysis-condensation of a first mixture having a tetra-alkoxysilane compound, an ethylenically unsaturated organosiloxane monomer, and a hydrophilic silicon-containing polyfunctional monomer. A hydrogel is prepared by polymerizing a second mixture having the aforesaid polysiloxane-based prepolymer, an acrylated silicon-containing monomer, and an ethylenically unsaturated hydrophilic monomer.

9 Claims, 4 Drawing Sheets

POLYSILOXANE-BASED PREPOLYMER AND HYDROGEL

CROSS-REFERENCE TO RELATED APPLICATION

This application claims priority of Taiwanese Application No. 096150791, filed on Dec. 28, 2007.

BACKGROUND OF THE INVENTION

1. Field of the Invention

The invention relates to a polysiloxane-based prepolymer, more particularly to a polysiloxane-based prepolymer having a three-dimensional network structure. The invention also relates to a hydrogel made from the aforesaid polysiloxane-based prepolymer and used for preparation of contact lenses.

2. Description of the Related Art

To improve oxygen permeability of contact lenses, silicone-containing hydrogel material is used in the preparation of contact lenses gradually. U.S. Pat. No. 5,387,632 discloses a contact lens made from a silicone-containing hydrogel material formed from a polymerization product of a monomer mix including (a) an acrylic-capped polysiloxane prepolymer represented by the formula:

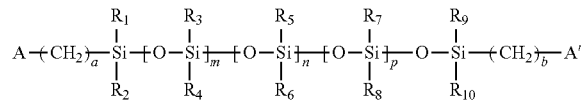

wherein A and A' are independently an ester or amide of an acrylic or methyacrylic acid; $R_1$ to $R_{10}$ are independently an alkyl, fluoroalkyl, alcohol, ether or fluoroether group having 1 to 10 carbons, or an aromatic group having 6-18 carbons; m, n, and p are independently 0 to 200 with m+n+p being from 23 to 200; and a and b are independently 1 to 10; (b) a bulky polysiloxanylalkyl(meth)acrylate monomer; and (c) at least one hydrophilic monomer.

U.S. Pat. No. 6,586,548 discloses a biocompatible copolymer produced by polymerizing a mixture having (a) at least one monomer selected from the group consisting of itaconates, (meth)acrylates, fumarates, and styrenics; (b) at least one monomer having a POSS compound including an ethylenically unsaturated radical; and (c) at least one ethylenically unsaturated organosiloxane monomer. Although the biocompatible copolymer exhibits superior toughness and sufficient oxygen permeability, the modulus thereof is greater than 1000 MPa, which undesirably reduces wear comfort.

Therefore, there remains a need for a hydrogel that exhibits sufficient oxygen permeability, wettability, and reduced modulus.

SUMMARY OF THE INVENTION

According to one aspect of this invention, a polysiloxane-based prepolymer of a three-dimensional network structure is produced by hydrolysis-condensation of a first mixture, the first mixture comprising:

(a) a tetra-alkoxysilane compound having the following formula (I):

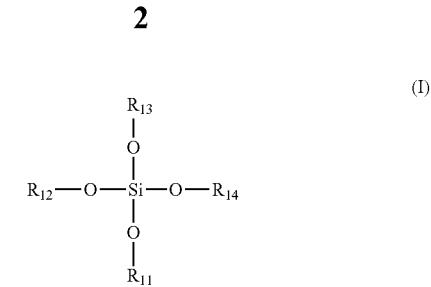

wherein $R_{11}$, $R_{12}$, $R_{13}$, and $R_{14}$ are independently a $C_1$-$C_8$ alkyl group;

(b) an ethylenically unsaturated organosiloxane monomer having the following formula (II):

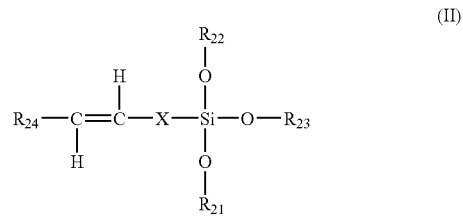

wherein $R_{21}$, $R_{22}$, and $R_{23}$ are independently a $C_1$-$C_6$ alkyl group, $R_{24}$ is a $C_1$-$C_6$ alkyl group, a cyano group, or hydrogen, and X is a $C_1$-$C_4$ alkylene, a single bond,

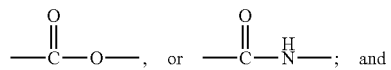

(c) a hydrophilic silicon-containing polyfunctional monomer having the following formula (III):

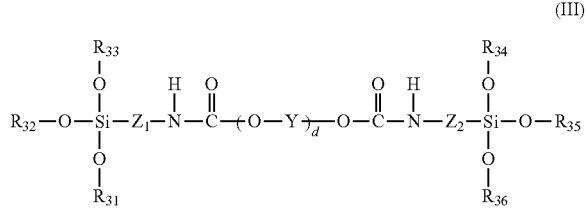

wherein Y is a $C_2$-$C_4$ alkylene group, $Z_1$ and $Z_2$ independently represent a single bond or a $C_1$-$C_4$ alkylene group, $R_{31}$, $R_{32}$, $R_{33}$, $R_{34}$, $R_{35}$, and $R_{36}$ independently represent a $C_1$-$C_6$ alkyl group, and d is an integer ranging from 3 to 90.

According to another aspect of this invention, a hydrogel is used for preparation of a contact lens and is produced by polymerizing a second mixture comprising:

(a) the aforesaid polysiloxane-based prepolymer;

(b) an acrylated silicon-containing monomer having the following formula (V):

(V)

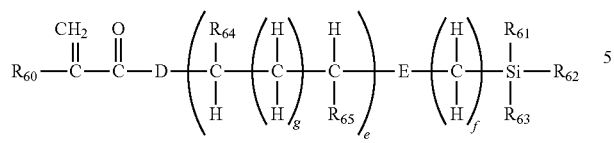

wherein: D represents O, NH, S or $CH_2$; E represents O or a single bond; $R_{60}$ represents H, $CH_3$, ph, $(CH_2)_iCH_3$, $CH(CH_3)_2$, $C(CH_3)_3$ or $Cph_2CH_3$; $R_{61}$, $R_{62}$, and $R_{63}$ independently represent H, $CH_3$, $(CH_2)_iCH_3$, $CH(CH_3)_2$, $C(CH_3)_3$, $Cph_2CH_3$, $O[Si(CH_3)_2O]_jSi(CH_3)_3$ or $OSiR_{66}R_{67}R_{68}$, where $R_{66}$, $R_{67}$, and $R_{68}$ independently represent H, $CH_3$ or $(CH_2)_i$ $CH_3$; $R_{64}$ and $R_{65}$ independently represent H, OH, $CH_3$, ph, $(CH_2)_iCH_3$, $CH(CH_3)_2$, $C(CH_3)_3$ or $Cph_2CH_3$; g is an integer from 0 to 2; e is an integer from 0 to 5; and f is an integer from 0 to 10; ph representing phenyl, i and j being independently integers from 1 to 10; and (c) an ethylenically unsaturated hydrophilic monomer.

BRIEF DESCRIPTION OF THE DRAWINGS

Other features and advantages of the present invention will become apparent in the following detailed description of the preferred embodiments of this invention, with reference to the accompanying drawings, in which.

DETAILED DESCRIPTION OF THE PREFERRED EMBODIMENTS

Figure 1:
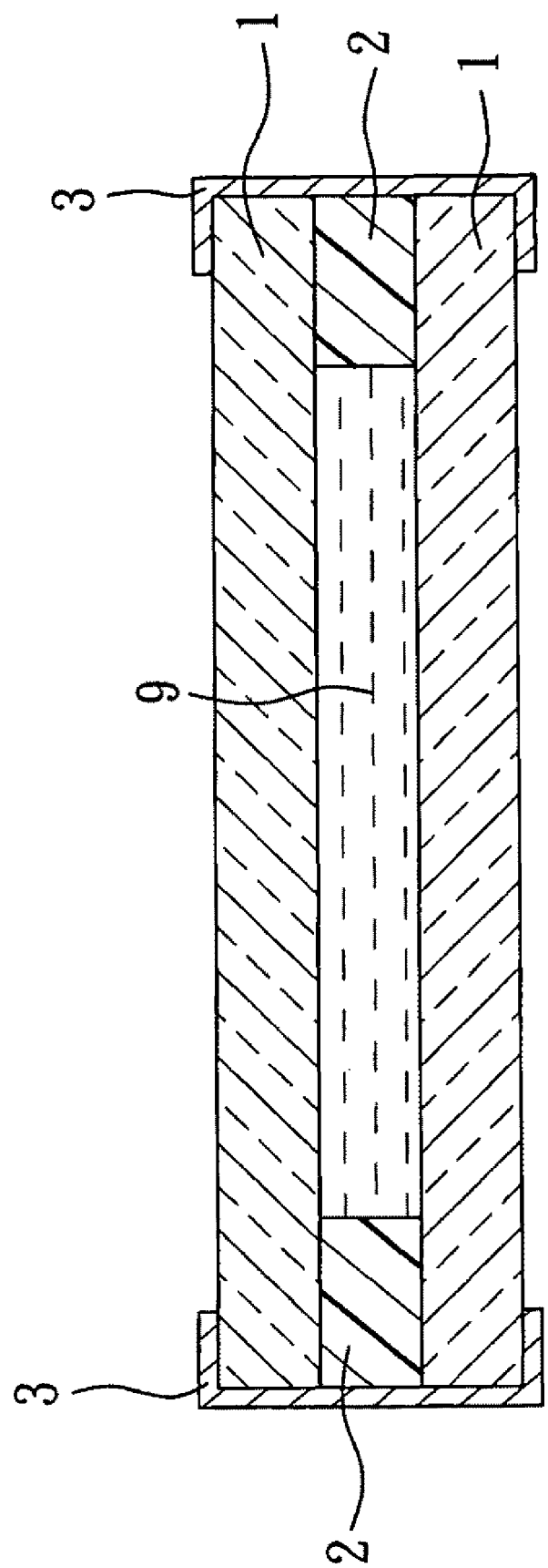
FIG. 1 shows a forming device used for preparation of the embodiment of a hydrogel sample according to this invention.

A polysiloxane-based prepolymer of a three-dimensional network structure according to the present invention is produced by hydrolysis-condensation of a first mixture that includes:

(a) a tetra-alkoxysilane compound having the following formula (I):

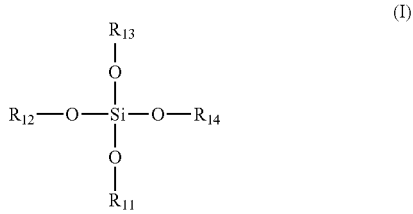

(I)

wherein $R_{11}$, $R_{12}$, $R_{13}$, and $R_{14}$ are independently a $C_1$-$C_8$ alkyl group;

(b) an ethylenically unsaturated organosiloxane monomer having the following formula (II):

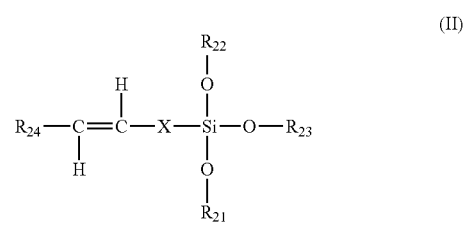

(II)

wherein $R_{21}$, $R_{22}$, and $R_{23}$ are independently a $C_1$-$C_6$ alkyl group; $R_{24}$ is a $C_1$-$C_6$ alkyl group, a cyano group, or hydrogen; and X is a $C_1$-$C_4$ alkylene, a single bond,

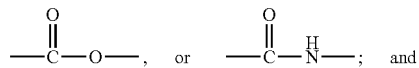

or (c) a hydrophilic silicon-containing polyfunctional monomer having the following formula (III):

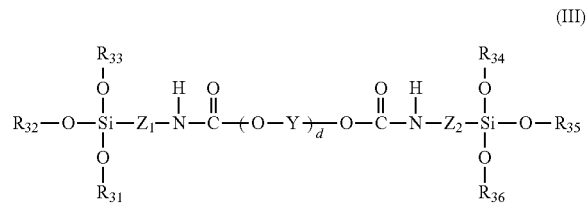

(III)

wherein Y is a $C_2$-$C_4$ alkylene group, $Z_1$ and $Z_2$ independently represent a single bond or a $C_1$-$C_4$ alkylene group, $R_{31}$, $R_{32}$, $R_{33}$, $R_{34}$, $R_{35}$, and $R_{36}$ independently represent a $C_1$-$C_6$ alkyl group, and d is an integer ranging from 3 to 90.

Preferably, the molar ratio of the hydrophilic silicon-containing polyfunctional monomer of formula (III) to tetra-alkoxysilane to the ethylenically unsaturated organosiloxane monomer is 1:2~22:2~40, more preferably 1:3~20:3~35, most preferably, 1:4~18:4~30. Within the molar ratio of 1:2~22:2~40, most of the unsaturated functional groups of the ethylenically unsaturated organosiloxane monomer will be at the surface of the polysiloxane-based prepolymer of the three-dimensional network structure after reaction, thereby providing reactive groups to facilitate subsequent polymerization for preparation of a hydrogel.

Preferably, the tetra-alkoxysilane compound is tetra-methoxysilane, tetra-ethoxysilane, or tetra-isopropoxysilane. In an example of this invention, the tetra-alkoxysilane compound is tetra-ethoxysilane.

Preferably, the ethylenically unsaturated organosiloxane monomer is vinyl trimethoxysilane, allyltrimethoxysilane, or 3-trimethoxysilyl propyl methacrylate. In an example of this invention, the ethylenically unsaturated organosiloxane monomer is vinyl trimethoxysilane.

Preferably, the hydrophilic silicon-containing polyfunctional monomer is prepared by reacting an isocyanate substituted (trialkoxy)silane represented by the following formula (IV):

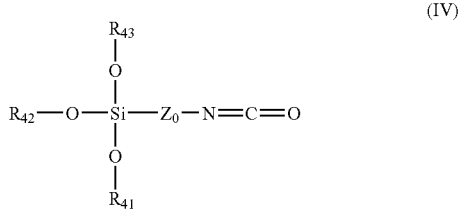

wherein $R_{41}$, $R_{42}$, and $R_{43}$ are independently a $C_1$-$C_6$ alkyl, and $Z_0$ is a single bond or a $C_1$-$C_4$ alkylene, with a polyether diol.

Preferably, the isocyanate substituted (trialkoxy)silane is isocyanatopropyltriethoxysilane or isocyanatopropyltrimethoxysilane.

Preferably, the polyether diol has a molecular weight ranging from 200 to 4,000, more preferably, from 350 to 2500. In an embodiment of this invention, the polyether diol is polyethylene glycol.

During polymerization, preferably, but not limitatively, the tetra-alkoxysilane compound is firstly mixed with the hydrophilic silicon-containing polyfunctional monomer, followed by addition of the ethylenically unsaturated organosiloxane monomer.

Optionally, if required, silanes, e.g., the trialkoxyl quaternary ammonium silane of product No. AB-8638 commercially available from Headway, and 1H,1H,2H,2H-perfluorooctyltriethoxysilane commercially available from Degussa, may be added to the first mixture to provide, e.g., anti-microbial and lipid-resistance properties for a hydrogel of this invention. The molar ratio of the hydrophilic silicon-containing polyfunctional monomer of formula (III) to tetra-alkoxysilane to the ethylenically unsaturated organosiloxane monomer to said additional silane is 1:2~22:2~40:0~10.

Preferably, the hydrolysis-condensation reaction is carried out under a pH value ranging from 2 to 5 or 8 to 12, preferably, 2 to 4 or 9 to 11, at a temperature ranging from 20 to 60° C., preferably, from 30 to 50° C. Preferably, the reaction is conducted for 4 to 24 hours, more preferably, 7 to 18 hours.

The polysiloxane-based prepolymer thus obtained can be used for the preparation of a hydrogel. The hydrogel of the present invention is a product of free radical chain polymerization of a second mixture. The second mixture includes:

(a) the aforesaid polysiloxane-based prepolymer;
(b) an acrylated silicon-containing monomer having the following formula (V):

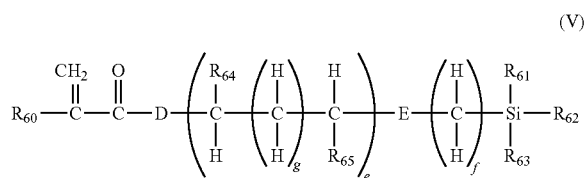

wherein D represents O, NH, S or $CH_2$; E represents O or a single bond; $R_{60}$ represents H, $CH_3$, ph, $(CH_2)_iCH_3$, $CH(CH_3)_2$, $C(CH_3)_3$ or $Cph_2CH_3$; $R_{61}$, $R_{62}$, and $R_{63}$ independently represent H, $CH_3$, $(CH_2)_iCH_3$, $CH(CH_3)_2$, $C(CH_3)_3$, $Cph_2CH_3$, $O[Si(CH_3)_2O]Si(CH_3)_3$ or $OSiR_{66}R_{67}R_{68}$, where $R_{66}$, $R_{67}$, and $R_{68}$ independently represent H, $CH_3$ or $(CH_2)_iCH_3$; $R_{64}$ and $R_{65}$ independently represent H, OH, $CH_3$, ph, $(CH_2)_iCH_3$, $CH(CH_3)_2$, $C(CH_3)_3$ or $Cph_2CH_3$; g is an integer from 0 to 2; e is an integer from 0 to 5; and f is an integer from 0 to 10; ph representing phenyl, i and j being independently integers from 1 to 10; and (c) an ethylenically unsaturated hydrophilic monomer.

Preferably, based on the total weight of the second mixture, the polysiloxane-based prepolymer is present in an amount ranging from 3 to 50 wt %, more preferably from 5 to 40 wt %, most preferably 10 to 30 wt %.

Preferably, based on the total weight of the second mixture, the acrylated silicon-containing monomer is present in an amount ranging from 10 to 50 wt %, more preferably from 15 to 40 wt %, most preferably from 20 to 30 wt %.

Preferably, based on the total weight of the second mixture, the ethylenically unsaturated hydrophilic monomer is present in an amount ranging from 20 to 60 wt %, more preferably from 30 to 50 wt %, most preferably from 35 to 45 wt %.

Preferably, examples of the acrylated silicon-containing monomer include: tris(trimethylsiloxy)silylpropyl methacrylate (TRIS), bis(trimethylsiloxy)methylsilylpropyl methacrylate, pentamethyldisiloxanepropyl methacrylate, pentamethyldisiloxanyl methylmethacrylate, tris(trimethylsiloxy)silylpropyloxyethyl methacrylate, tris(trimethylsiloxy)silylpropyl methacryloxyethylcarbamate, tris(trimethylsiloxy)silylpropyl glycerol methacrylate (SIGMA), and tris(polydimethylsiloxy)silylpropyl methacrylate. In an example of this invention, the acrylated silicon-containing monomer is tris(trimethylsiloxy)silylpropyl methacrylate.

Preferably, examples of the ethylenically unsaturated hydrophilic monomer include: hydroxyethyl methacrylate (HEMA), methacrylic acid (MAA), N-vinylpyrrolidone (NVP), N,N'-dimethylacrylamide (DMA), N,N'-diethylacrylamide, N-isopropylacrylamide, 2-hydroxyethyl acrylate, vinyl acetate, N-acryloylmorpholine, and 2-dimethylaminoethyl acrylate. In the examples of this invention, the ethylenically unsaturated hydrophilic monomers are HEMA, NVP, and DMA.

Preferably, the second mixture further includes a linear silicone-containing prepolymer having the following formula (VI):

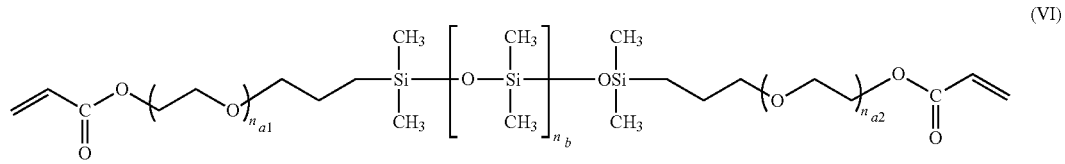

wherein $n_{a1}/n_b$=0~1.5, $n_{a2}/n_b$=0~5, and $n_b$ is an integer ranging from 4 to 50.

In addition, in the reaction of the free radical chain polymerization of the second mixture, based on the weight of the second mixture, 0.2 to 1 wt % of a photo-initiator or a thermal initiator can be used. The photo-initiator and the thermal initiator may be any currently known initiator, e.g., those disclosed in U.S. Pat. No. 6,992,118 and U.S. Pat. No. 5,908,906. 2-Hydroxy-2-methyl-1-pentyl-1-propanone is used as a photo-initiator in an embodiment of this invention.

When a photo-initiator is used, preferably, the free radical chain polymerization is conducted under an irradiation condition ranging from 2 mw/cm$^2$ to 10 mw/cm$^2$, preferably from 2 mw/cm$^2$ to 5 mw/cm$^2$. When a thermal initiator is used, preferably, the heat treatment temperature is from 60° C. to 120° C. Preferably, the time of irradiation or heat treatment ranges from 10 minutes to 2 hours, more preferably from 30 minutes to 2 hours.

The hydrogel of this invention can be used for preparation of contact lenses. According to several known techniques for manufacturing contact lenses, the casting process may yield a shaped article having the desired posterior and anterior lens surfaces. For example, in static casting processes, the second mixture can be charged to a mold having a first mold section and a second mold section for forming desired anterior and posterior lens surface, respectively. In spin casting processes, the second mixture can be charged to an open mold having a surface for forming a desired anterior lens surface. The desired posterior lens surface is formed from rotation of the mold. However, machining operations, subsequent to the curing of the article, may still be necessary to provide a contact lens more suitable for placement on the eye. Such machining operations include lathe cutting the lens to obtain a desired edge, buffering the lens edge or polishing the lens edge or surface.

The hydrogel of this invention can be used for preparing an eye implant, such as an intraocular lens, or a cornea replacement, such as artificial cornea. When used as an eye implant, aromatic-containing silicone segment can be introduced during synthesis of the polysiloxane-based prepolymer. Alternatively, during preparation of the hydrogel, benzene compounds may be added to enhance the refractive index of the eye implant formed therefrom.

EXAMPLES

Sources of Chemicals

1. Polyethylene glycol (PEG): commercially available from Fluka, CAS no. 25322-68-3, molecular weight 1000.
2. 3-isocyanatopropyltriethoxysilane (IPTS): Silquest® A-link™ 25 silane commercially available from GE silicones, CAS no. 24801-88-5.
3. Dibutyltin dilaurate: commercially available from TCI, CAS no. 77-58-7.
4. Tetraethoxysilane (TEOS): commercially available from SHOWA, CAS no. 78-10-4.
5. Trialkoxyl quaternary ammonium silane (represented by AB-silane in the following Table 1): commercially available from Headway, product no. AB-8638, molecular weight 1400.6.
6. 1H,1H,2H,2H-perfluorooctyltriethoxysilane (CF$_3$(CF$_2$)$_5$CH$_2$CH$_2$Si(OC$_2$H$_5$)$_3$, represented by F-silane in Table 1): commercially available from Degussa, CAS no. 51851-37-7.
7. Vinyl trimethoxysilane: commercially available from Topco Technology Corp., product no. KBM1003.
8. Hydrophilic silicon-containing polyfunctional monomer represented by formula (S): prepared according to the steps of this invention as described in the following example.
9. Acrylated siloxane polyalkyleneoxide copolymer (a linear silicone-containing prepolymer): CoatOsil® 3509 commercially available from GE silicones.
10. Tris(trimethylsiloxy)silylpropyl methacrylate (TRIS): commercially available from Gelest, CAS no. 17096-07-0.
11. N-vinylpyrrolidone (NVP): commercially available from ALDRICH, CAS no. 88-12-0.
12. Hydroxyethyl methacrylate (HEMA): commercially available from ACROS, CAS no. 868-77-9.
13. N,N'-dimethylacrylamide (DMA): commercially available from TCI, CAS no. 0680-3-7.

Equipment

1. Nuclear Magnetic Resonance spectrometer (NMR): commercially available from Bruker; model no. ADVANCED 300.
2. Fourier Transform Infrared spectrometer (FT-IR) commercially available from Perkin Elmer; model no T1.

General Method

1. Contact angle analysis was carried out according to a sessile drop method.
2. Water content percentage test was measured according to ISO standard 10339.
3. Oxygen permeability was measured according to ISO 9913-1.
4. Elongation and tensile modulus were measured according to ASTM D1780.
5. Cytotoxicity tests were conducted in accordance with the method described in ISO 10993-5: Biological Evaluation of Medical Devices-Test for in vitro cytotoxicity.

Preparation of Hydrophilic Silicon-Containing Polyfunctional Monomer 30 g (≈0.03 mol) of polyethylene glycol and 14.82 g of 3-isocyanatopropyltriethoxysilane were allowed to react at a temperature of 70° C. and under nitrogen condition, and dibutyltin dilaurate in an amount that is 0.3 wt % of the total weight of the two aforesaid ingredients was simultaneously added as a catalyst. The reaction lasted for 1~3 hours, and purification was conducted using hexane so as to remove unreacted monomers. Finally, drying was conducted at a temperature from 40° C. to 60° C. under vacuum conditions, thereby obtaining a dried hydrophilic silicon-containing polyfunctional monomer. The purified hydrophilic silicon-containing polyfunctional monomer was identified using NMR and FT-IR.

The result determined by NMR is as follows:

$^1$H-NMR (300 MHz, CDCl$_3$), δ5.02 (br, 1H, NH), 4.2~4.12 (m, 2H, —CH$_2$ of urethane), 3.78 (Quat, J=6.9 Hz, 6H, —OCH$_2$—), 3.61 (s, 40H, —OCH$_2$CH$_2$O— of PEG), 3.17~3.04 (m, 2H, N—CH$_2$— of urethane), 1.62~1.52 (m, 2H, —CH$_2$—), 1.18 (t, J=6.9 Hz, 9H, —CH$_3$—), 0.65~0.52 (m, 2H, —CH$_2$—Si—).

In addition, a comparison of the IR spectra before and after the reaction reveals that a peak representing —N═C═O at around 2200 cm$^{-1}$ of the IR spectrum of the reactants prior to reaction has disappeared from the spectrum after reaction. Moreover, after reaction, since N═C═O and —OH at the terminal end of PEG will react to form NH—(C═O)—, a peak representing C═O was generated at ~1700 cm$^{-1}$ of the IR spectrum after reaction. In addition, from the ratio value of 4.2~4.12 (m, 2H, —CH$_2$ of urethane) intensity to 3.61 (s, 40H, —OCH$_2$—CH$_2$—O— of PEG) intensity, it can be estimated that the molecular weight of the hydrophilic silicon-containing polyfunctional monomer is from 1400 to 1662.

In addition, the results determined by FT-IR and NMR indicate that the product is a hydrophilic silicon-containing polyfunctional monomer represented by the following formula (S):

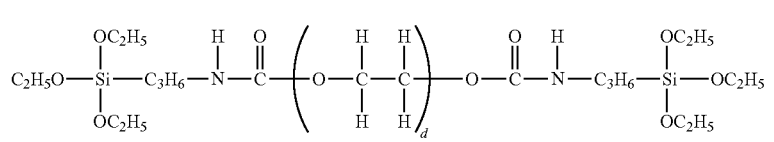

wherein d is an integer ranging from 21 to 27.

Preparation of Polysiloxane-Based Prepolymer

Example 1

Preparation Steps (1) 6.9 g of the dried hydrophilic silicon-containing polyfunctional monomer and 4.6 g of TEOS were mixed in a round-bottomed flask at ambient temperature, and a suitable amount of isopropanol was added thereto, thereby obtaining a clear and transparent reaction solution.

(2) The reaction solution obtained in step (1) was heated to 40° C., and 1080 μl aqueous hydrochloride ($HCl_{(aq)}$) with a pH of 2~3 was added thereto to conduct a first hydrolysis-condensation polymerization for about 3 hours.

(3) 6.3 g of vinyl trimethoxysilane was slowly added to the reaction solution that underwent the first hydrolysis-condensation polymerization in step (2), and 1140 μl of aqueous hydrochloride with a pH of 2~3 was further added to conduct a second hydrolysis-condensation polymerization for 6 hours, thereby obtaining a first solution (solid content=0.45 g/ml) having silicone-containing prepolymers dispersed therein.

(4) Isopropanol in the reaction solution having undergone the second hydrolysis-condensation polymerization in step (3) was removed using vacuum concentration at 50° C. Purification was conducted using hexane to obtain the polysiloxane-based prepolymer of the present invention, and hexane was subsequently removed using vacuum concentration, thereby obtaining a purified polysiloxane-based prepolymer of the present invention.

Structure Identification:

The structure of the polysiloxane-based prepolymer thus obtained was identified using NMR and FT-IR. The NMR results are: $^1$H-NMR (300 MHz, $CDCl_3$), δ6.18~5.82 (m, 3H, $CH_2$=CH—), 4.2~4.17 (m, 1H, —$CH_2$ of urethane), 3.79 (Quat, J=5.6 Hz, 3H, $SiOCH_2$—), 3.62 (s, 26H, —$OCH_2CH_2O$— of PEG), 3.17~3.12 (m, 1H, N—$CH_2$— of urethane), 1.63~1.53 (m, 1H, —$CH_2$—), 1.29~1.23 (m, 3H), 1.22 (t, J=5.6 Hz, 4.5H, —$CH_3$), 0.65~0.56 (m, 1H, —$CH_2$—Si—). In addition, absorption signals of $CH_2$=CH— double bond are clearly visible at 1600.64 $nm^{-1}$ and around 800 $nm^{-1}$ of the IR spectrum.

While the NMR and IR results might not be sufficient for completely figuring out the structure of the polysiloxane-based prepolymer of this invention, they could clearly show that the aforesaid reactants did undergo hydrolysis-condensation polymerization. In addition, the polysiloxane-based prepolymer of this invention has a three-dimensional network 3D structure having a granular size ranging from 1 nm to 400 nm, preferably from 5 nm to 300 nm.

Examples 2 to 6

The steps for preparing the polysiloxane-based prepolymer according to this invention in examples 2 to 6 are substantially the same as those of example 1. The differences reside in the amounts of the aqueous hydrochloride, and the types and amounts of the reactants. The operating conditions of the examples are shown in Table 1. In addition, AB-silane was further added in step (1) of example 4, and F-silane was further added in step (1) of example 6.

TABLE 1

| | Hydrophilic polyfunctional monomer prepared by this invention (g/mole) | Tetra-alkoxy-silane compound TEOS (g/mole) | Silane | | ethylenically unsaturated organosiloxane monomer | Aqueous HCL $HCl_{(aq)}$ of | Aqueous HCL $HCl_{(aq)}$ of |
|---|---|---|---|---|---|---|---|
| | | | AB-silane (g/mole) | F-silane (g/mole) | vinyl trimethoxysilane (g/mole) | steps (2) (μl) | step (3) (μl) |
| Ex. 1 | 6.9/0.0042 | 4.6/0.0221 | 0 | 0 | 6.3/0.0423 | 1080 | 1140 |
| Ex. 2 | 6.9/0.0042 | 4.6/0.0221 | 0 | 0 | 3.15/0.0211 | 1080 | 570 |
| Ex. 3 | 10.61/0.0064 | 7.07/0.0340 | 0 | 0 | 3.2/0.0214 | 1655 | 585 |
| Ex. 4 | 4.5/0.0027 | 3/0.0144 | 6/0.0019 | 0 | 4.4/0.0295 | 755 | 800 |
| Ex. 5 | 2.7/0.0016 | 7.3/0.0351 | 0 | 0 | 8/0.0537 | 1375 | 1470 |
| Ex. 6 | 5.11/0.0031 | 3.45/0.0166 | 0 | 0.675/0.0013 | 8/0.0537 | 1375 | 1470 |

Experiment: Preparation of Hydrogel Samples

Experiment 1

The operating steps of this experiment are as follows:

(1) A suitable amount of the first solution having polysiloxane-based prepolymers of the present invention dispersed therein, which was obtained in step (3) of example 1, was mixed homogeneously with CoatOsil®, TRIS, and the ethylenically unsaturated hydrophilic monomers into a second solution, such that the content ratios of the polysiloxane-based prepolymers, CoatOsil®, TRIS, and the ethylenically unsaturated hydrophilic monomers are approximately 13.16 wt %, 10.86 wt %, 21.7 wt %, and 54.28 wt %, respectively.

The ethylenically unsaturated hydrophilic monomers include three types of monomers, namely NVP, HEMA and DMA, at a weight ratio of 2.5/1/1.5.

(2) Into the second solution obtained in step (1) was added 0.7% 2-hydroxy-2-methyl-1-pentyl-1-acetone (manufacturer: CIBA; model no.: D1173) based on the weight of the second mixture, and a small amount of isopropanol so as to obtain a mixed solution.

(3) The mixed solution obtained in step (2) was injected into a forming device (as shown in FIG. 1) having two glass clamping plates 1 arranged parallel to each other, a silicone pad 2 disposed between the clamping plates 1 and adjacent to four peripheral edges of each of the clamping plates 1, and two securing members 3 for holding the clamping plates 1 and the silicone pad 2 in place such that the mixed solution 9 was surrounded by the clamping plates 1 and the silicone pad 2. Photo-initiation was subsequently conducted for 1 hour under light intensity from 2 to 3 mw/cm$^2$ so as to form a silicone-containing gel sheet.

(4) The securing members 3, the clamping plates 1, and the silicone pad 2 were detached in sequence, and the gel sheet was removed and immersed in a mixed solution of alcohol/H$_2$O at a ratio of 7/3 for 1 to 2 hours for extraction, and was subsequently immersed in saline for 1 to 2 hours, thereby obtaining the hydrogel of this invention.

(5) The hydrogel was subjected to heat treatment at 121° C. for 30 minutes for sterilization, thereby obtaining a hydrogel test sample.

Experiments 2 to 10

The steps for preparing the hydrogel samples in experiments 2 to 10 are substantially similar to those in experiment 1, except for the amounts and types of the reactants. The amounts and types of the reactants for experiments 1 to 10 are shown in the following Table 2.

Comparative Experiment 1

The steps for preparing the hydrogel sample in comparative example 1 were substantially the same as those in experiment 1. The major differences reside in that the polysiloxane-based prepolymer according to the present invention was not included, and that, in step 1, about 13.42 wt % of CoatOsil®, about 26.18 wt % of TRIS, and about 60.4 wt % of the ethylenically unsaturated hydrophilic monomers were mixed homogeneously, and that the weight ratio of NVP/HEMA (i.e., the ethylenically unsaturated hydrophilic monomers) was 4.5/1.5.

Comparative Experiment 2

The steps for preparing the hydrogel sample in comparative example 2 were substantially the same as those in experiment 1, except that the polysiloxane-based prepolymer according to the present invention was not included, and that, in step 1, about 22.73 wt % of CoatOsil®, about 31.82 wt % of TRIS and about 45.45 wt % of the ethylenically unsaturated hydrophilic monomers were mixed homogeneously, and that the weight ratio of NVP/HEMA (i.e., the ethylenically unsaturated hydrophilic monomers) was 19/6.

TABLE 2

|  | Polysiloxane-based prepolymer (wt %) | Linear silicone-containing pre-polymer CoatOsil (wt %) | Acrylated silicon-containing monomer TRIS (wt %) | Ethylenically unsaturated hydrophilic monomer (wt %) (NVP/HEMA/DMA) (weight ratio) |
|---|---|---|---|---|
| Experiment 1 | Example 1 13.16 | 10.86 | 21.7 | 54.28 (2.5/1/1.5) |
| Experiment 2 | Example 1 13.16 | 10.86 | 21.7 | 54.28 (3.5/1.5/0) |
| Experiment 3 | Example 2 13.16 | 10.86 | 21.7 | 54.28 (3.5/1.5/0) |
| Experiment 4 | Example 3 13.16 | 10.86 | 21.7 | 54.28 (3.5/1.5/0) |
| Experiment 5 | Example 4 13.12 | 10.86 | 21.72 | 54.3 (7/3/0) |
| Experiment 6 | Example 2 9 | 18.2 | 27.3 | 45.5 (19/6/0) |
| Experiment 7 | Example 2 13.64 | 13.64 | 27.27 | 45.45 (19/6/0) |
| Experiment 8 | Example 2 18.18 | 9.1 | 27.27 | 45.45 (19/6/0) |
| Experiment 9 | Example 2 18.18 | 18.19 | 27.27 | 36.36 (4.7/1.3/0) |
| Experiment 10 | Example 2 13.42 | 0 | 26.18 | 60.4 (4.5/1.5/0) |
| Comparative example 1 | 0 | 13.42 | 26.18 | 60.4 (4.5/1.5/0) |
| Comparative example 2 | 0 | 22.73 | 31.82 | 45.45 (19/6/0) |

Analysis for Contact Angle, Water Content Percentage and Oxygen-Permeability

The samples obtained in experiments 1 to 8 and comparative examples 1 and 2 were respectively subjected to contact angle analysis, and tests for water content percentage and oxygen permeability. The contact angle analysis characterizes the wettability of the hydrogel sample. The results of the tests are shown in Table 3.

The contact angle of materials currently used for making a contact lens is from 10° to 90°. It is shown in Table 3 that the contact angles of the hydrogel samples of this invention are from 30° to 60°, and are therefore in compliance with current requirements. The hydrogel samples have water content of from 40% to 60%, and oxygen permeability of from 30 Dk to 60 Dk.

TABLE 3

|  | Contact angle (°) | Water content (wt %) | Oxygen permeability (Dk) |
|---|---|---|---|
| Experiment 1 | — | 46 | 35.23 ± 2.66 |
| Experiment 2 | 53.2 | 47.22 | 42.05 ± 1.24 |
| Experiment 3 | 56 | 48.5 | 43.5 ± 1.24 |
| Experiment 4 | 44 | 54.1 | — |
| Experiment 5 | 53.2 | 42.43 | 35.16 ± 2.05 |
| Experiment 6 | 43.2 | 42.82 | 54.39 ± 5.63 |
| Experiment 7 | 42 | 42.44 | 45.8 ± 3.17 |
| Experiment 8 | 36 | 44.42 | 41.22 ± 5.1 |
| Experiment 9 | 58 | 37.77 | 46.39 ± 1.54 |
| Experiment 10 | 56.78 | 54.26 | 29.31 ± 1.6 |
| Comparative example 1 | 58.6 | 44.35 | 49.43 ± 1.10 |
| Comparative example 2 | 94 | 38.93 | 95 ± 5.22 |

Remark:
The symbol "—" represents measurement not taken.

Mechanical Property Test

The hydrogel samples (thickness=0.4 mm) obtained in experiments 1 to 3, experiments 5 to 8, experiment 10, and comparative examples 1 and 2 were measured for elongation and tensile modulus according to ASTM D1780. The results are shown in the following table 4.

As shown in Table 4, the tensile moduli of the hydrogel samples according to the present invention are lower than 1 Mpa. Therefore, the contact lens formed therefrom has better wear comfort. In addition, the elongation of all the samples is over 150%. It is especially noted that, as shown in Tables 3 and 4, although the values of oxygen permeability of comparative examples 1 and 2 are higher than those of experiments 1 to 8, the elongation of comparative examples 1 and 2 are merely 76.853% and 58.55% (see Table 2), which indicates that comparative examples 1 and 2 have poorer durability. This manifests that the present invention is less likely to break when subjected to an external stretching force, and has better durability.

TABLE 4

| | Expt. 1 | Expt. 2 | Expt. 3 | Expt. 4 | Expt. 5 | Expt. 6 | Expt. 7 | Expt. 8 | Expt. 10 | Comp. ex. 1 | Comp. ex. 2 |
|---|---|---|---|---|---|---|---|---|---|---|---|
| Elongation (%) | 236 | 156.29 | 253 | 262.13 | 173.03 | 165 | 171.6 | 236.4 | 176.67 | 76.853 | 58.55 |
| Tensile modulus (Mpa) | 0.75 | 0.79 | 0.553 | 0.309 | 0.617 | 0.596 | 0.729 | 0.68 | 0.644 | 0.552 | 0.636 |

Cytotoxicity Test

Cytotoxicity tests were conducted with respect to the samples obtained in experiment 6. According to the biological evaluation, a zone index and a lysis index were calculated by observing the number and morphology of cells and with reference to the index definitions ISO 10993-5. Thereafter, a response index (RI) value was calculated from the two indices using the formula (RI=zone index/lysis index). The lower the RI value, the lower would be the cytotoxicity.

The samples used in the cytotoxicity tests include: (1) a sample with a diameter of 1.1 cm cut from the hydrogel according to the present invention obtained in experiment 6; (2) a sample of the same size which was immersed in 1% of phenol solution and used as a positive control; and (3) a polytetrafluoroethylene (PTFE) sample used as a negative control.

First, L-929 fibroblasts were diluted in minimal essential medium (MEM) containing 10% of fetal bovine serum (FBS) to $1\times10^5$ cells/ml, followed by inoculation into a 6-well culture plate, 2 ml per well. Subsequently, the culture was cultivated in an incubator set at a temperature of 37° C. and filled with 5% of $CO_2$ for 24 hours. Thereafter, the MEM was removed, and 2 ml of agar medium (in the form of liquid) heated to 45° C. was added to each well of the 6-well culture plate. When the temperature of the agar medium dropped to room temperature, the agar medium would coagulate, thereby obtaining a cell-containing solid agar medium.

Figure 2:
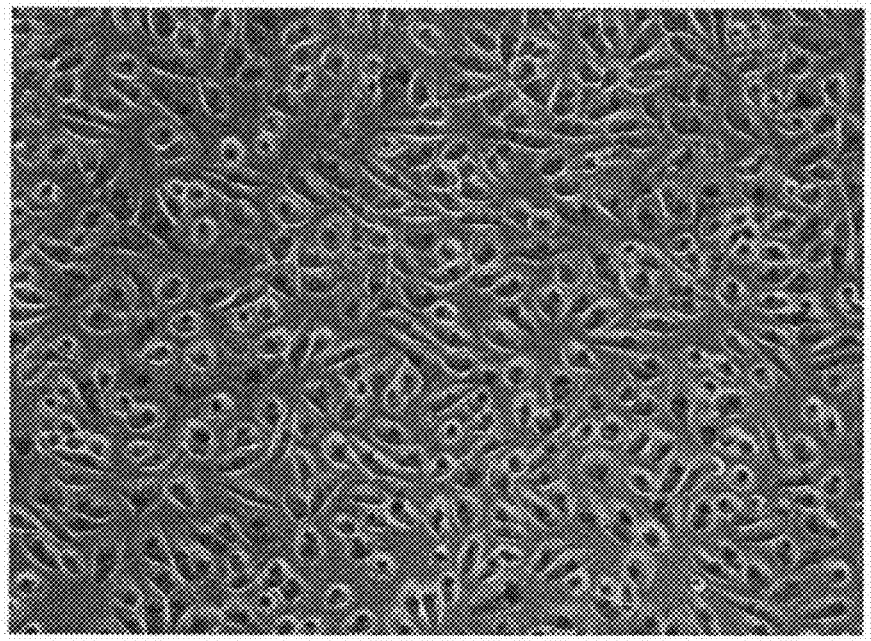
FIG. 2 is an image to show the cells in a sample zone for the hydrogel sample according to this invention.
Figure 3:
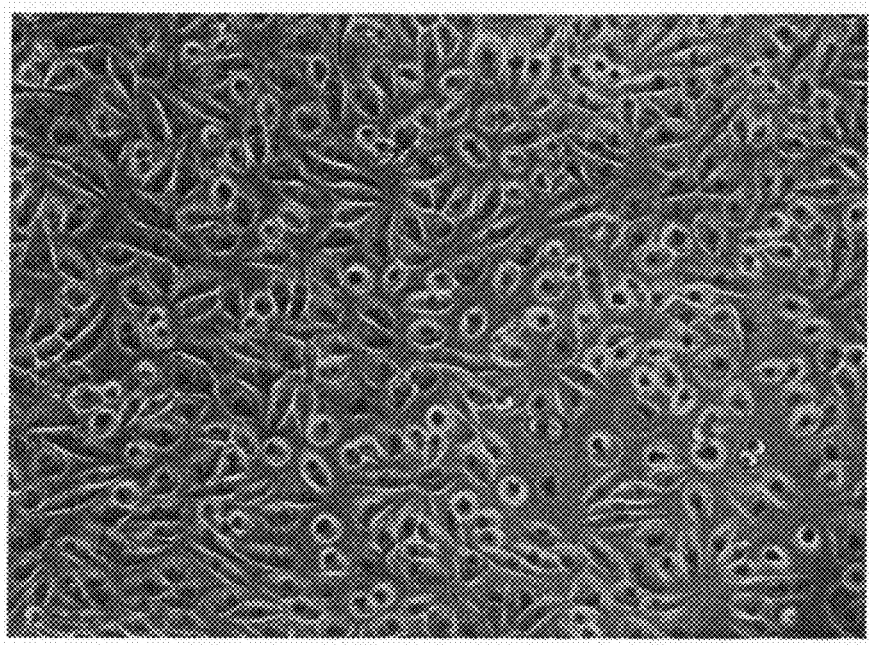
FIG. 3 is an image to show the cells in a diffusion zone for the hydrogel sample according to this invention.
Figure 4:
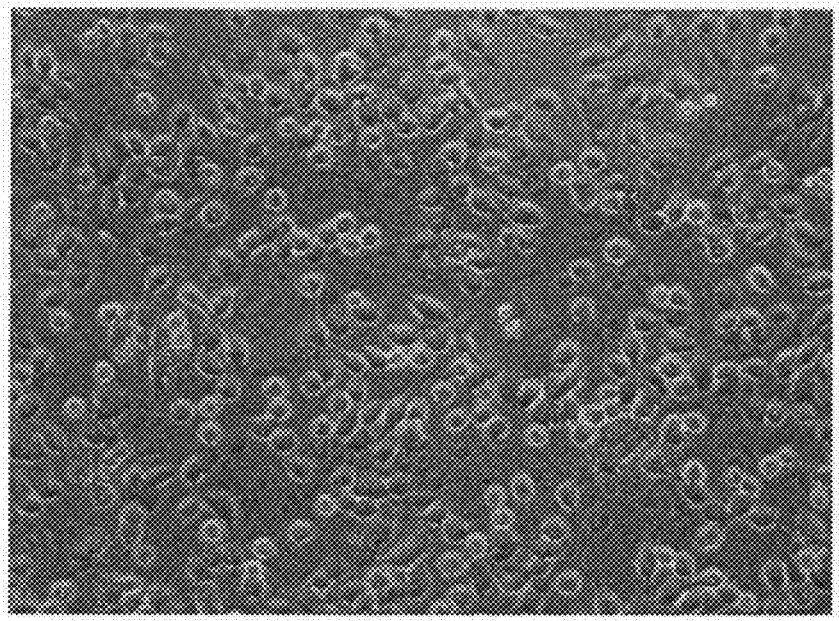
FIG. 4 is an image to show the cells in a sample zone for a positive control sample.
Figure 5:
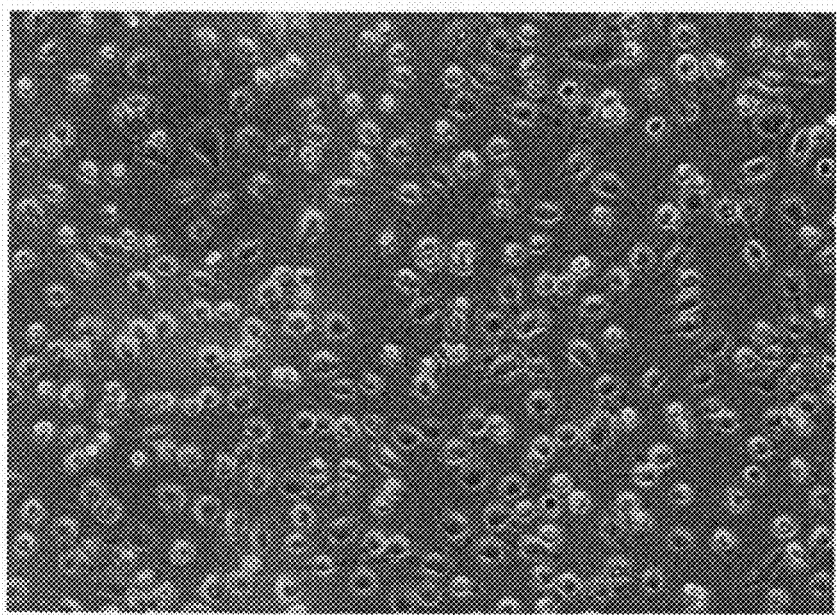
FIG. 5 is an image to show the cells in a diffusion zone for the positive control sample.
Figure 6:
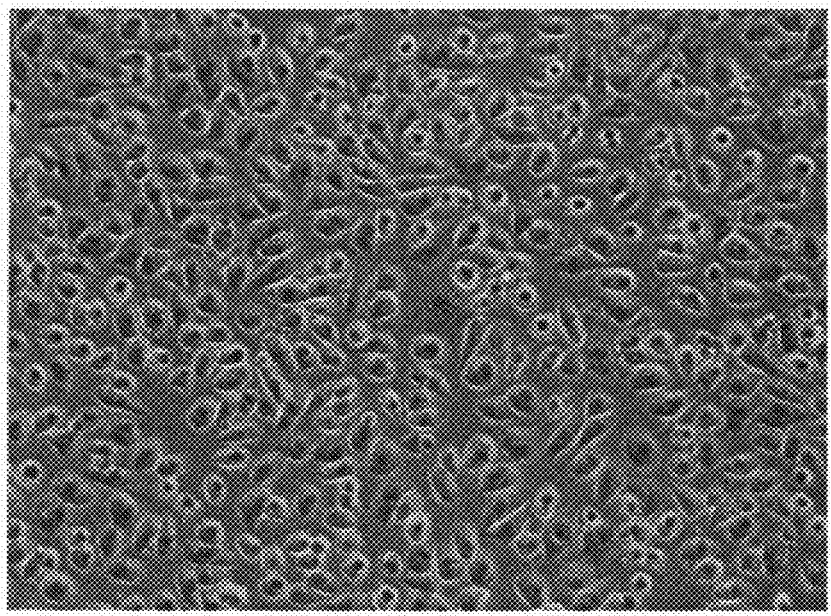
FIG. 6 is an image to show the cells in a sample zone for a negative control sample.
Figure 7:
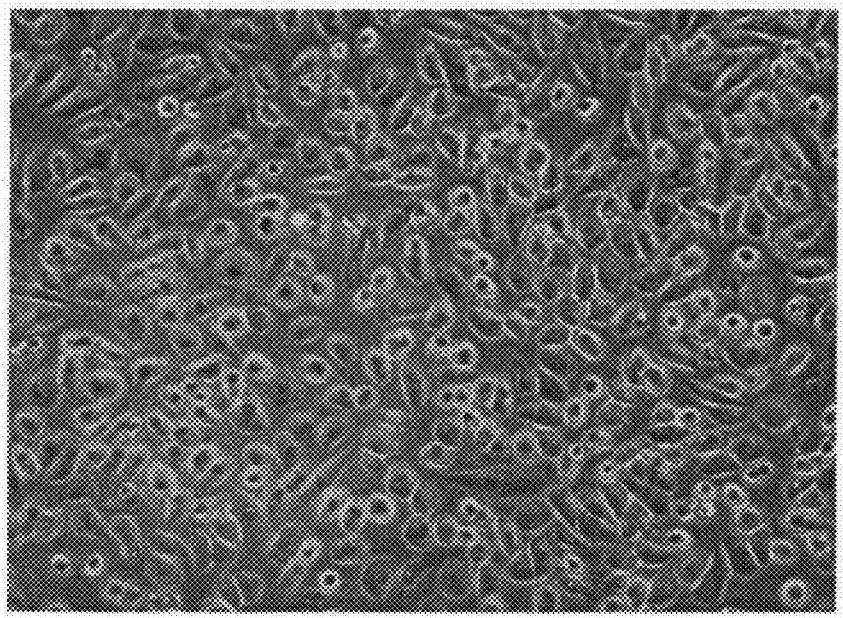
FIG. 7 is an image to show the cells in a diffusion zone for the negative control sample.

Subsequently, the hydrogel sample of this invention obtained in experiment 6, the positive control sample, and the negative control sample were respectively placed on the cell-containing agar media and were cultivated in an incubator set at 37° C. and filled with 5% of $CO_2$ for 24 hours. On the back of each well of the culture plate at a position corresponding to each of the samples, a profile of the sample and a circle concentric with the profile and having a radius greater than that of the profile were drawn. The area within the profile was a sample zone, and the area outside the profile and within the circle was a diffusion zone. Thereafter, each sample was removed from the surface of the agar medium, and the agar medium was stained using a neutral red solution. Subsequently, the number and morphology of the cells in the sample zones and the diffusion zones were observed under an inverted microscope set at 200× magnification. The experimental results are shown in FIGS. 2 to 7. FIGS. 2 and 3 are, respectively, images of the stained cells in the sample zone and the diffusion zone for experiment 6. FIGS. 4 and 5 are, respectively, images of the stained cells in the sample zone and the diffusion zone for the positive control samples. FIGS. 6 and 7 are, respectively, images of the stained cells in the sample zone and the diffusion zone for the negative control samples.

A zone index and a lysis index were calculated for each sample from the number and morphology of the cells in the sample zones and the diffusion zones for the hydrogel samples obtained in experiment 6, the positive control samples, and the negative control samples, and a response index was calculated from the two indices. The response indices for experiment 6, and the positive and negative controls are 0/0, 5/5 and 0/0. The results show that the hydrogel of this invention passed the cell cytotoxicity test in accordance with ISO 10993-5, and is therefore non-toxic.

In sum, the values of the contact angle, water content, and oxygen permeability obtained for the hydrogel samples according to the present invention meet the standards required by current contact lenses. Moreover, the elongation and tensile modulus data of the samples also indicate that the samples provide good wear comfort and durability. It is evident that the polysiloxane-based prepolymer made from the hydrophilic silicon-containing polyfunctional monomer of the present invention provides the hydrogel sample formed therefrom with good wettability and oxygen permeability, and desirable mechanical properties (e.g., tensile modulus and elongation). Furthermore, the hydrogel of this invention also passes the cell cytotoxicity test in accordance with ISO 10993-5.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A polysiloxane-based prepolymer of a three-dimensional network structure produced by hydrolysis-condensation of a first mixture, said first mixture comprising:
    (a) a tetra-alkoxysilane compound having the following formula (I):

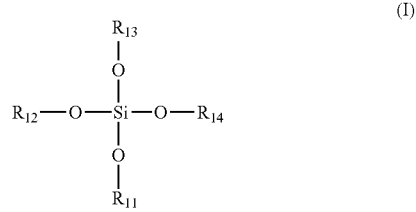

wherein $R_{11}$, $R_{12}$, $R_{13}$, and $R_{14}$ are independently a $C_1$-$C_8$ alkyl group;

(b) an ethylenically unsaturated organosiloxane monomer having the following formula (II):

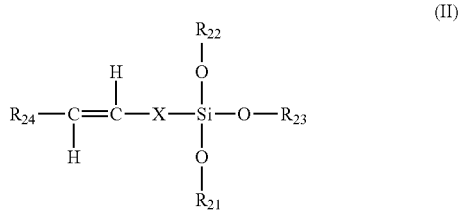

wherein $R_{21}$, $R_{22}$, and $R_{23}$ are independently a $C_1$-$C_6$ alkyl group, and $R_{24}$ is a $C_1$-$C_6$ alkyl group, a cyano group, or hydrogen, and X is a $C_1$-$C_4$ alkylene, a single bond,

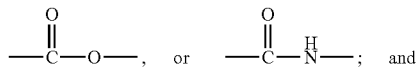

(c) a hydrophilic silicon-containing polyfunctional monomer having the following formula (III):

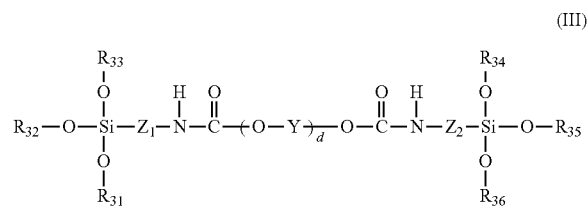

wherein Y is a $C_2$-$C_4$ alkylene group, $Z_1$ and $Z_2$ independently represent a single bond or a $C_1$-$C_4$ alkylene group, $R_{31}$, $R_{32}$, $R_{33}$, $R_{34}$, $R_{35}$, and $R_{36}$ independently represent a $C_1$-$C_6$ alkyl group, and d is an integer ranging from 3 to 90.

2. The polysiloxane-based prepolymer of claim 1, wherein the molar ratio of said hydrophilic silicon-containing polyfunctional monomer to tetra-alkoxysilane to said ethylenically unsaturated organosiloxane monomer in the first mixture is 1:2~22:2~40.

3. The polysiloxane-based prepolymer of claim 1, wherein tetra-alkoxysilane is tetraethoxysilane.

4. The polysiloxane-based prepolymer of claim 1, wherein said ethylenically unsaturated organosiloxane monomer is vinyl trimethoxysilane.

5. A hydrogel used for preparation of contact lenses and produced by polymerizing a second mixture, said second mixture comprising:

(a) a polysiloxane-based prepolymer of claim 1;

(b) an acrylated silicon-containing monomer having the following formula (V):

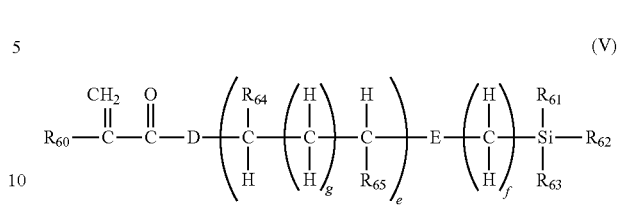

wherein D represents O, NH, S or $CH_2$; E represents O or a single bond; $R_{60}$ represents H, $CH_3$, ph, $(CH_2)_iCH_3$, $CH(CH_3)_2$, $C(CH_3)_3$ or $Cph_2CH_3$; $R_{61}$, $R_{62}$, and $R_{63}$ independently represent H, $CH_3$, $(CH_2)_iCH_3$, $CH(CH_3)_2$, $C(CH_3)_3$, $Cph_2CH_3$, $O[Si(CH_3)_2O]_jSi(CH_3)_3$ or $OSiR_{66}R_{67}R_{68}$, where $R_{66}$, $R_{67}$, and $R_{68}$ independently represent H, $CH_3$ or $(CH_2)_iCH_3$; $R_{64}$ and $R_{65}$ independently represent H, OH, $CH_3$, ph, $(CH_2)_iCH_3$, $CH(CH_3)_2$, $C(CH_3)_3$ or $Cph_2CH_3$; g is an integer from 0 to 2; e is an integer from 0 to 5; and f is an integer from 0 to 10; ph representing phenyl, i and j being independently integers from 1 to 10; and (c) an ethylenically unsaturated hydrophilic monomer.

6. The hydrogel of claim 5, wherein, based on the total weight of said second mixture, said polysiloxane-based prepolymer is present in an amount ranging from 3 to 50 wt %.

7. The hydrogel of claim 5, wherein said acrylated silicon-containing monomer is selected from the group consisting of: tris(trimethylsiloxy)silylpropyl methacrylate, bis(trimethylsiloxy)methylsilylpropyl methacrylate, pentamethyldisiloxanepropyl methacrylate, pentamethyldisiloxanyl methylmethacrylate, tris(trimethylsiloxy)silylpropyloxyethyl methacrylate, tris(trimethylsiloxy)silylpropyl methylacryloxyethylcarbamate, tris(trimethylsiloxy)silylpropyl glycerol methacrylate, tris(polydimethylsiloxy)silylpropyl methacrylate, and combinations thereof.

8. The hydrogel of claim 5, wherein said ethylenically unsaturated hydrophilic monomer is selected from the group consisting of: hydroxyethyl methacrylate, methacrylic acid, N-vinyl pyrrolidone, N,N'-dimethylacrylamide, N,N'-diethylacrylamide, N-isopropylacrylamide, 2-hydroxyethyl acrylate, vinyl acetate, N-acryloyl morpholine, 2-dimethylaminoethyl acrylate, and combinations thereof.

9. The hydrogel of claim 5, wherein said second mixture further includes a linear silicone-containing prepolymer having the following formula (VI):

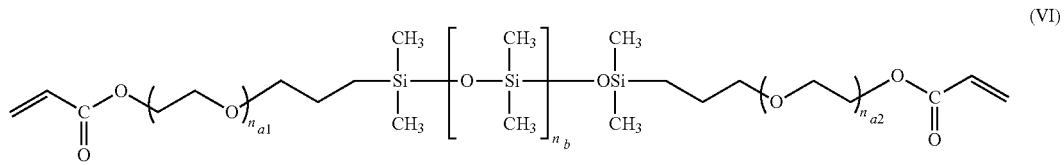

wherein $n_{a1}/n_b$=0~1.5, $n_{a2}/n_b$=0~1.5, and $n_b$ is an integer ranging from 4 to 50.

* * * * *